(12) United States Patent
Hon

(10) Patent No.: US 8,863,752 B2
(45) Date of Patent: *Oct. 21, 2014

(54) ELECTRONIC CIGARETTE

(71) Applicant: Fontem Holdings 1 B.V., Amsterdam (NL)

(72) Inventor: Lik Hon, North Point (HK)

(73) Assignee: Fontem Holdings 1 B.V., Amsterdam (NL)

(*) Notice: Subject to any disclaimer, the term of this patent is extended or adjusted under 35 U.S.C. 154(b) by 0 days.

This patent is subject to a terminal disclaimer.

(21) Appl. No.: 13/915,427

(22) Filed: Jun. 11, 2013

(65) Prior Publication Data

US 2013/0276798 A1    Oct. 24, 2013

Related U.S. Application Data

(63) Continuation of application No. 13/754,521, filed on Jan. 30, 2013, which is a continuation of application No. 12/226,819, filed as application No. PCT/CN2007/001576 on May 15, 2007, now Pat. No. 8,375,957.

(51) Int. Cl.
  *A24F 1/32*   (2006.01)
  *A24F 47/00*   (2006.01)

(52) U.S. Cl.
  CPC ............. *A24F 47/002* (2013.01); *A24F 47/004* (2013.01); *A24F 47/008* (2013.01)
  USPC ........................ 131/194; 131/270; 128/202.21

(58) Field of Classification Search
  USPC ................................................. 131/194, 270
  See application file for complete search history.

(56) References Cited

U.S. PATENT DOCUMENTS

| | | | |
|---|---|---|---|
| 705,919 | A | 7/1902 | Gill |
| 1,775,947 | A | 9/1930 | Robinson |
| 2,057,353 | A | 10/1936 | Whittemore |
| 2,631,219 | A | 3/1953 | Suchy |

(Continued)

FOREIGN PATENT DOCUMENTS

| | | |
|---|---|---|
| CN | 2047485 U | 11/1989 |
| CN | 2084236 U | 9/1991 |

(Continued)

OTHER PUBLICATIONS

CB Distributors Inc. and DR Distributors, LLC , Petition for Inter Partes Review of US Patent No. 8,156,944 and Exhibits 1-20, filed Jun. 27, 2013.

(Continued)

*Primary Examiner* — Richard Crispino
*Assistant Examiner* — Dionne Walls Mayes
(74) *Attorney, Agent, or Firm* — Kenneth H. Ohriner; Perkins Coie LLP

(57) ABSTRACT

An electronic cigarette includes a battery assembly, an atomizer assembly and a cigarette bottle assembly. An external thread electrode is located in one end of battery assembly. An internal thread electrode is located in one end of atomizer assembly. The battery assembly and the atomizer assembly are connected by the screwthread electrode. The cigarette bottle assembly is inserted into the other end of the atomizer assembly and both form a cigarette type or cigar type body.

20 Claims, 10 Drawing Sheets

(56) References Cited

U.S. PATENT DOCUMENTS

| | | |
|---|---|---|
| 3,200,819 A | 8/1965 | Gilbert |
| 3,551,643 A | 12/1970 | Pricenski et al. |
| 4,171,000 A | 10/1979 | Uhle |
| 4,207,457 A | 6/1980 | Haglund et al. |
| 4,228,925 A | 10/1980 | Mendelovich |
| 4,641,053 A | 2/1987 | Takeda |
| 4,735,217 A | 4/1988 | Gerth et al. |
| 4,756,318 A | 7/1988 | Clearman et al. |
| 4,771,796 A | 9/1988 | Myer |
| 4,819,665 A | 4/1989 | Roberts et al. |
| 4,848,374 A | 7/1989 | Chard et al. |
| 4,945,929 A | 8/1990 | Egilmex |
| 4,945,931 A | 8/1990 | Gori |
| 4,947,875 A | 8/1990 | Brooks et al. |
| 5,042,470 A | 8/1991 | Kanesaka |
| 5,060,671 A | 10/1991 | Counts et al. |
| 5,080,114 A | 1/1992 | Rudolph et al. |
| 5,095,921 A | 3/1992 | Losee et al. |
| 5,144,962 A | 9/1992 | Counts et al. |
| 5,159,940 A | 11/1992 | Hayward et al. |
| 5,190,060 A | 3/1993 | Gerding et al. |
| 5,224,498 A | 7/1993 | Deevi et al. |
| 5,249,586 A | 10/1993 | Morgan et al. |
| 5,261,424 A | 11/1993 | Sprinkel, Jr. |
| 5,285,798 A | 2/1994 | Banerjee et al. |
| 5,322,075 A | 6/1994 | Deevi et al. |
| 5,388,594 A | 2/1995 | Counts et al. |
| 5,438,978 A | 8/1995 | Hardester, III |
| 5,497,791 A | 3/1996 | Bowen et al. |
| 5,505,214 A | 4/1996 | Collins et al. |
| 5,591,368 A | 1/1997 | Fleischhauer et al. |
| 5,666,977 A | 9/1997 | Higgins et al. |
| 5,666,978 A | 9/1997 | Counts et al. |
| 5,730,158 A | 3/1998 | Collins et al. |
| 5,743,251 A | 4/1998 | Howell et al. |
| 5,746,251 A | 5/1998 | Bullard |
| 5,799,663 A | 9/1998 | Gross et al. |
| 5,819,756 A | 10/1998 | Mielordt |
| 5,878,752 A | 3/1999 | Adams et al. |
| 5,894,841 A | 4/1999 | Voges |
| 6,040,560 A | 3/2000 | Fleischhauer et al. |
| 6,041,789 A | 3/2000 | Bankert et al. |
| 6,095,153 A | 8/2000 | Kessler et al. |
| 6,164,287 A | 12/2000 | White |
| 6,178,969 B1 | 1/2001 | St. Charles |
| 6,196,218 B1 | 3/2001 | Voges |
| 6,354,293 B1 | 3/2002 | Madison |
| 6,357,671 B1 | 3/2002 | Cewers |
| 6,443,146 B1 | 9/2002 | Voges |
| 6,532,965 B1 | 3/2003 | Abhulimen et al. |
| 6,601,776 B1 | 8/2003 | Oljaca et al. |
| 6,715,494 B1 | 4/2004 | McCoy |
| 6,772,756 B2 | 8/2004 | Shayan |
| 6,803,545 B2 | 10/2004 | Blake et al. |
| 6,810,883 B2 | 11/2004 | Felter et al. |
| 6,854,461 B2 | 2/2005 | Nichols et al. |
| 6,854,470 B1 | 2/2005 | Pu |
| 7,100,618 B2 | 9/2006 | Dominguez |
| 7,131,599 B2 | 11/2006 | Katase |
| 7,726,320 B2 | 6/2010 | Robinson et al. |
| 7,832,410 B2 | 11/2010 | Hon |
| 7,845,359 B2 | 12/2010 | Montaser |
| 7,997,280 B2 | 8/2011 | Rosenthal |
| 8,156,944 B2 | 4/2012 | Hon |
| 2003/0108342 A1 | 6/2003 | Sherwood et al. |
| 2004/0182403 A1 | 9/2004 | Andersson et al. |
| 2004/0261802 A1 | 12/2004 | Griffin et al. |
| 2005/0016550 A1 | 1/2005 | Katase |
| 2005/0236006 A1 | 10/2005 | Cowan |
| 2006/0196518 A1 | 9/2006 | Hon |
| 2008/0276947 A1 | 11/2008 | Martzel |
| 2009/0095311 A1 | 4/2009 | Han |
| 2009/0126745 A1 | 5/2009 | Hon |
| 2009/0151717 A1 | 6/2009 | Bowen et al. |
| 2009/0188490 A1 | 7/2009 | Han |
| 2009/0230117 A1 | 9/2009 | Fernando et al. |
| 2009/0260642 A1 | 10/2009 | Monsees et al. |
| 2009/0272379 A1 | 11/2009 | Thorens et al. |
| 2010/0031968 A1 | 2/2010 | Sheikh et al. |
| 2010/0126505 A1 | 5/2010 | Rinker |
| 2010/0181387 A1 | 7/2010 | Zaffaroni et al. |
| 2010/0200008 A1 | 8/2010 | Taieb |
| 2010/0242974 A1 | 9/2010 | Pan |
| 2010/0307518 A1 | 12/2010 | Wang |
| 2011/0005535 A1 | 1/2011 | Xiu |
| 2011/0011396 A1 | 1/2011 | Fang |
| 2011/0036346 A1 | 2/2011 | Cohen et al. |
| 2012/0111347 A1 | 5/2012 | Hon |

FOREIGN PATENT DOCUMENTS

| | | |
|---|---|---|
| CN | 1135860 | 11/1996 |
| CN | 1196660 A | 11/1996 |
| CN | 1196660 A | 10/1998 |
| CN | 2293957 Y | 10/1998 |
| CN | 1252961 A | 5/2000 |
| CN | 1575673 A | 2/2005 |
| CN | 2719043 Y | 8/2005 |
| CN | 2719043 Y | 10/2005 |
| CN | 2777995 Y | 5/2006 |
| CN | 2887086 U | 4/2007 |
| CN | 200997909 Y | 1/2008 |
| CN | 101116542 A | 2/2008 |
| CN | 101176805 A | 5/2008 |
| CN | 201067079 Y | 6/2008 |
| CN | 201079011 Y | 7/2008 |
| CN | 201379072 Y | 1/2010 |
| CN | 201797997 U | 4/2011 |
| CN | 202026802 U | 11/2011 |
| CN | 202026804 U | 11/2011 |
| DE | 10051792 A1 | 5/2002 |
| EP | 0057243 A1 | 8/1982 |
| EP | 0230420 A1 | 8/1987 |
| EP | 0295122 B1 | 12/1988 |
| EP | 0342538 A2 | 11/1989 |
| EP | 0358002 A2 | 3/1990 |
| EP | 0545186 A2 | 6/1993 |
| EP | 0703735 A1 | 4/1996 |
| EP | 0824927 A2 | 2/1998 |
| EP | 0845220 A1 | 6/1998 |
| EP | 0893071 A1 | 1/1999 |
| EP | 0951219 A1 | 10/1999 |
| GB | 1528391 A | 10/1978 |
| JP | 64000498 U | 1/1989 |
| JP | 06114105 A | 4/1994 |
| JP | 07506999 | 8/1995 |
| JP | 09075058 A | 3/1997 |
| UA | 47514 | 12/1997 |
| WO | WO-9409842 A1 | 5/1994 |
| WO | WO-9421317 A1 | 9/1994 |
| WO | WO-9740876 A2 | 11/1997 |
| WO | WO-9748293 A1 | 12/1997 |
| WO | WO-9817130 A1 | 4/1998 |
| WO | WO-0049901 A2 | 8/2000 |
| WO | WO-0050111 A1 | 8/2000 |
| WO | WO-0105459 A1 | 1/2001 |
| WO | WO-03022364 A1 | 3/2003 |
| WO | WO-03034847 A1 | 5/2003 |
| WO | WO-03055486 A1 | 7/2003 |
| WO | WO-03101454 A1 | 12/2003 |
| WO | WO-2004001407 A1 | 12/2003 |
| WO | WO-2004023222 | 3/2004 |
| WO | WO-2004080216 | 9/2004 |
| WO | 2005099494 A | 10/2005 |
| WO | WO-2006082571 | 8/2006 |
| WO | WO-2007078273 | 7/2007 |
| WO | WO-2008077271 | 7/2008 |
| WO | WO-2008130813 | 10/2008 |
| WO | WO-2009118085 | 10/2009 |
| WO | WO-2009135729 | 11/2009 |
| WO | WO-2010052323 | 5/2010 |
| WO | WO-2010145468 | 12/2010 |

(56) References Cited

FOREIGN PATENT DOCUMENTS

| | | |
|---|---|---|
| WO | WO-2010145805 | 12/2010 |
| WO | WO-2011010334 | 1/2011 |
| WO | WO-2011022431 | 2/2011 |

OTHER PUBLICATIONS

Pan, Fenglin—Request for Invalidation of CN200720148285.9 in Chinese, along with English translation of same (citing D1-CN2719043 and D2 CN2084236), filed Jun. 19, 2013.
Chen, Zhiyong; English Translation of Claim Charts Accompanying Request to Invalidate CN Utility Model Patent No. 200620090805.0 (citing D1-200420031182.0 and D2-CN 97190727.7), Jun. 6, 2013.
CN Creative ; Intellicig USA, *Ruyan* v. *Smoking Everywhere et al.* CV11-6268 Invalidity Contentions, Apr. 12, 2012.
Cyphert, GIL DBA NU1S, *Ruyan* v. *Smoking Everywhere et al.* CV11-0367 Invalidity Contentions, Apr. 11, 2012.
European Patent Office, extended European Search Report for EP 07721148, Dec. 6, 2010.
European Patent Office, extended European Search Report for EP 11001479, Jul. 4, 2011.
European Patent Office, Supplementary European Search Report for EP04718242, Jul. 27, 2007.
European Patent Office, Supplementary European Search Report for EP05729107, Jul. 31, 2007.
European Patent Office, Supplementary Partial European Search Report for EP04718242, May 22, 2007.
European Patent Office, Supplementary Partial European Search Report for EP05729107, May 22, 2007.
FIN Branding Group, LLC, Request for Inter Partes Reexamination of U.S. Patent No. 8,156,944, filed Sep. 13, 2012.
FIN Branding Group, LLC, Submission of Prior Art and Miscellaneous Statement Pursuant to 376 C.F.R. §1.948, Feb. 27, 2013.
Introduction to Selecting and Using Electronic Components, ISBN7-111-13752-3.
IP Australia, Examination Report for SG 200505930-8, May 4, 2006.
IP Australia, Patent Examination Report No. 1 for AU2007250367, Jul. 30, 2012.
IP Australia, Patent Examination Report No. 1 for AU2007250368, Aug. 9, 2012.
IP Australia; Exam Report for AU2004234199, Aug. 14, 2009.
IP Australia; Search and Examination Report for SG200604498-6, Apr. 16, 2008.
Japanese Patent Office; Office Action for JP2006504199, Oct. 30, 2009.
Korean Patent Office; Notice of Preliminary Rejection for KR1020057009767, Jul. 27, 2009.
Macau Patent Office; Official Communication for MOI121, Apr. 17, 2009.
Machine translation Chinese Patent Application 200420031182 which corresponds to the priority document of WO20051099494 (HON '494) Oct. 27, 2005, cited by the Examiner in the Nov. 27, 2012 Office Action identified above.
European Patent Office, Supplementary European Search Report and Search Opinion for EP 10740882.5, Oct. 16, 2013. (Note counterpart US20090188490 of cited EP2018886 and counterpart US20090095311 of cited WO2007131449 are already of record. Counterpart US2011011396 of cited CN101606758 is listed above.).
European Patent Office, Third Party Observation for EP Application No. 10740882, filed by Anonymous on Oct. 3, 2013. (Note counterpart US5144962 of cited EP0430559 is already of record.).
IP Australia, Patent Examination Report No. 1 for AU 2010213240, Aug. 5, 2013. (Note counterpart US20090188490 of cited CN200966824 is already of record.).
Pan, Fenglin—Request for Invalidation of CN200920001296.3 in Chinese, along with English translation of same (citing D1-CN2887086Y (listed above), D2-CN1040914A (counterpart US4947875 is already of record), and D3-CN201067079Y (listed above), Jun. 20, 2013.
State Intellectual Property Office, P.R. China, Office Action for CN201080016105.6, Aug. 30, 2013, with English translation. (Note counterpart US20090188490 of cited CN200966824 and counterpart US5144962 of cited EP0430559 are already of record.).
Machine translation of Chinese Patent Application 03111582.9 which corresponds to the priority document of WO2004/095955 (HON '955) Nov. 11, 2004, cited by the Examiner in the Nov. 27, 2012 Office Action identified above.
Malaysia Intellectual Property Office; Examiner's Report for Malaysian Application No. PI 20041407, Sep. 28, 2007.
Manual for Electric Engineers, 2nd Edition, Mar. 2000.
Manual for Mechanical Designers, 4th Edition, Jan. 2002.
Materials Manual—Nonmetal, Jul. 1985.
Sottera, Inc., *Ruyan* v. *Smoking Everywhere et al.* CV11-0367 Invalidity Contentions, Apr. 12, 2012.
Sottera, Inc., *Ruyan* v. *Smoking Everywhere et al.* CV11-0367 Invalidity Contentions, Exhibit 7 (Claim 20 Claim Chart), Apr. 12, 2012.
Sottera, Inc., *Ruyan* v. *Smoking Everywhere et al.* CV11-0367 Invalidity Contentions, Exhibit 8 (Claim 24 Claim Chart), Apr. 12, 2012.
State Intellectual Property Office (China), English Translation of the Written Opinion for PCT/CN07/001575, Jul. 20, 2007.
State Intellectual Property Office (China), English Translation of the Written Opinion for PCT/CN07/001576, Aug. 3, 2007.
State Intellectual Property Office (China), International Search Report for International Application No. PCT/CN2004000182, Jun. 10, 2004.
State Intellectual Property Office (China), International Search Report for International Application No. PCT/CN2005/000337, Jul. 14, 2005.
State Intellectual Property Office (China), International Search Report for PCT/CN07/001575, Aug. 16, 2007.
State Intellectual Property Office (China), International Search Report for PCT/CN07/001576, Aug. 16, 2007.
State Intellectual Property Office International Search Report for PCT/CN10/073613, Aug. 26, 2010.
State Intellectual Property Office, International Search Report for PCT/CN10/000125, Apr. 1, 2010.
State Intellectual Property Office, Search Report for Utility Model Patent ZL 200620090805.0, Nov. 18, 2008.
Taiwan Intellectual Property Office; Official Letter for TW093111573, Apr. 24, 2009.
TechPowerUp, "What is a MOSFET, what does it look like, and how does it work?",http://www.techpowerup.com/articles/overclocking/voltmods/21, dated May 24, 2004, printed from the Internet of Jun. 4, 2011, 3 pages.
Ukrainian Patent Office; Examination Report for UA200511258, Feb. 4, 2009.
United States Patent and Trademark Office, Office Action in Inter Partes Reexamination of U.S. Patent No. 8,156,944, mailed Nov. 27, 2012.
PRB of the State Intellectual Patent Office, Decision of Patent Invalidation Petition (No. 22179) issued in Chinese Patent Application No. 200620090805.0 (Mar. 3, 2014).
State Intellectual Property Office of the People's Republic of China, Examination Decision of the Patent Re-examination Board on the Invalidity Declaration Application issued in Chinese Patent Application No. 200620090805.0 (Jun. 23, 2010).
Njoy, Inc. et al., Defendants' Joint Invalidity Contentions, Case No. CV-14-01645 etc., Aug. 7, 2014.
Njoy, Inc. et al., Attachment D to Defendant's Joint Invalidity Contentions—Claim Charts for Patent 8375957, Aug. 7, 2014.

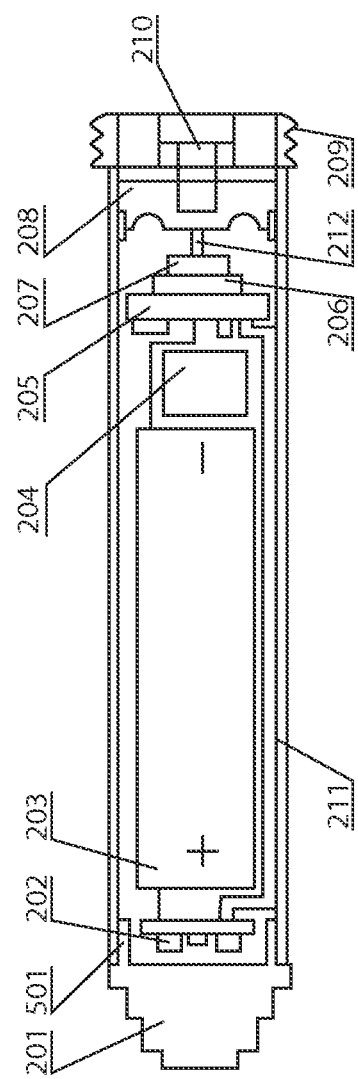

ELECTRONIC CIGARETTE

CROSS-REFERENCE TO RELATED APPLICATIONS

This application is a continuation of U.S. patent application Ser. No. 13/754,521, filed Jan. 30, 2013 and now pending, which is a continuation of U.S. patent application Ser. No. 12/226,819, filed Jan. 15, 2009, now U.S. Pat. No. 8,375,957, which is a 371 national phase application of International Patent Application No. PCT/CN2007/001576, filed May 15, 2007 and now converted, which claims the benefit of Chinese Patent Application No. 200620090805.0, filed May 16, 2006. All of these applications are incorporated herein by reference in their entirety.

BACKGROUND

Although smoking causes serious respiratory diseases and cancers, it is difficult to get smokers to quit smoking. Nicotine is the effective ingredient in cigarettes. Nicotine is a micromolecular alkaloid which is basically harmless to humans at low dosages. Tar is the major harmful substance in tobacco. Tobacco tar contains thousands of ingredients, dozens of which are carcinogenic.

Cigarette substitutes have used relatively pure nicotine in patches, chewing gum and aerosols. Still disadvantages remain with cigarette substitutes or products for helping smokers to quit smoking.

SUMMARY OF THE INVENTION

An improved electronic cigarette has a battery assembly, an atomizer assembly and a cigarette bottle assembly. The battery assembly connects with one end of the atomizer assembly, and the cigarette bottle assembly is inserted into the other end of the atomizer assembly, thus forming one cigarette type or cigar type body. Use of the electronic cigarette reduces cancer risks and fire hazards while providing a simulated smoking experience.

BRIEF DESCRIPTION OF DRAWINGS

FIG. 2B is a view of another battery assembly.

DETAILED DESCRIPTION OF THE DRAWINGS

Figure 1:
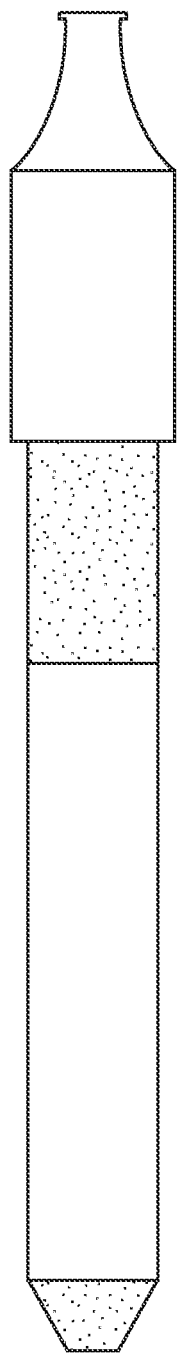
FIG. 1 is a side view of an electronic cigarette.
Figure 2A:
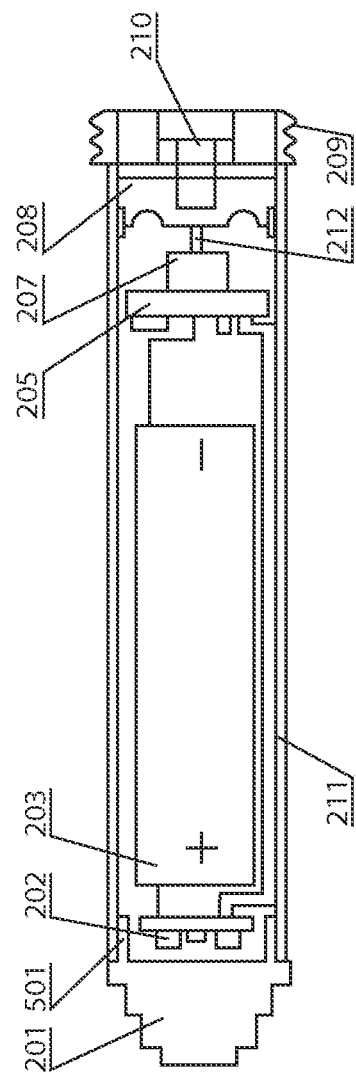
FIG. 2A is a view of the battery assembly.

As shown in FIG. 1, an electronic cigarette has an appearance similar to a cigarette inserted into the cigarette holder. As shown in FIG. 2A, the electronic cigarette includes a battery assembly, an atomizer assembly and a cigarette bottle assembly. An external thread electrode (209) is located in one end of the battery assembly, and an internal thread electrode (302) is located in one end of the atomizer assembly. The battery assembly and atomizer assembly are connected through the screw thread electrode into an electronic cigarette. The cigarette bottle assembly is inserted into the other end of atomizer assembly.

As shown in FIG. 2A, the battery assembly includes an indicator (202), lithium ion battery (203), MOSFET electric circuit board (205), sensor (207), silica gel corrugated membrane (208), primary screw thread electrode (209), primary negative pressure cavity (210), and primary shell (211). On one end of the primary shell (211) is an external thread electrode (209). On the other end is an indicator (202), where there is an indicator cap (201) on one side having a small hole (501). On the other side, the lithium ion battery (203) and MOSFET (Metallic Oxide Semiconductor Field Effect Tube) electric circuit board (205) are connected successively. The sensor (207) is located on MOSFET electric circuit board (205). Between the primary screw thread electrode (209) and sensor (207) is a silica gel corrugated membrane (208), on which there is the primary negative pressure cavity (210). The sensor (207) is connected with the silica gel corrugated membrane (208) through the switch spring (212).

The sensor (207) may be switch sensor made of elastic alloy slice, a linear output Hall sensor, a semiconductor force-sensitive chip, a semiconductor matrix thermoelectric bridge chip, capacitance or inductance sensor. The indicators (202) include two red LEDs. The lithium ion battery (203) may be either a rechargeable polymer lithium ion battery or a rechargeable lithium ion battery. The external thread electrode (209) is a gold-coated stainless steel or brass part with a hole drilled in the center. The silica gel corrugated membrane (208) may alternatively be made of fluorinated rubber, butyronitrile rubber, or elastic alloy film.

Figure 3:
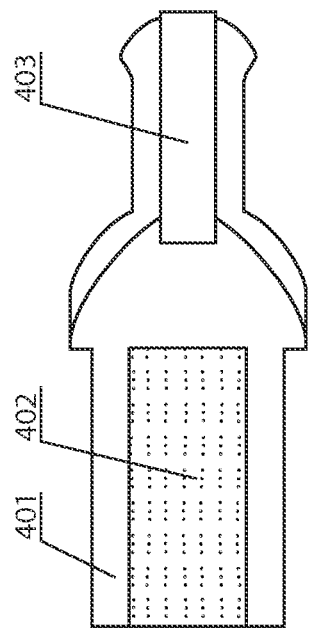
FIG. 3 is the diagram of the atomizer assembly.

As shown in FIG. 3, the atomizer assembly includes the internal thread electrode (302), air-liquid separator (303), atomizer (307) and the secondary shell (306). One end of the secondary shell (306) is inserted into the cigarette bottle assembly for connection, while the other end has an internal thread electrode (302), in which there is the secondary negative pressure cavity (301). The air-liquid separator (303) and the atomizer (307) are connected with the internal thread electrode (302) successively. On the secondary shell (306), there is an air intake hole (502). The air-liquid separator (303) is made of stainless steel or plastic with a hole. The internal thread electrode (302) is a gold-coated stainless steel or brass part with a hole in the center.

Figure 4:
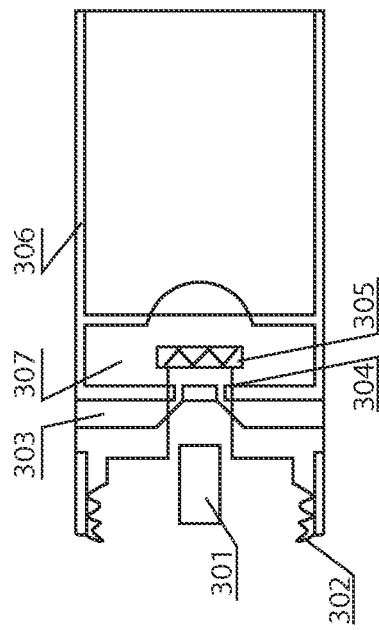
FIG. 4 is the diagram of the cigarette bottle assembly.
Figure 8:
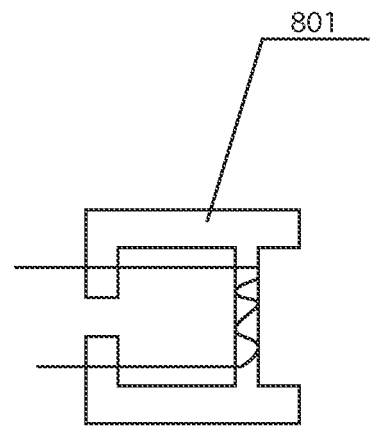
FIG. 8 is a side view of an atomizer.
Figure 9:
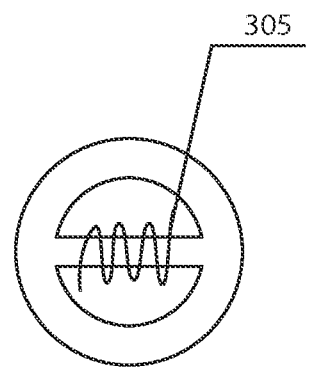
FIG. 9 is an end view of the atomizer shown in FIG. 8.
Figure 10:
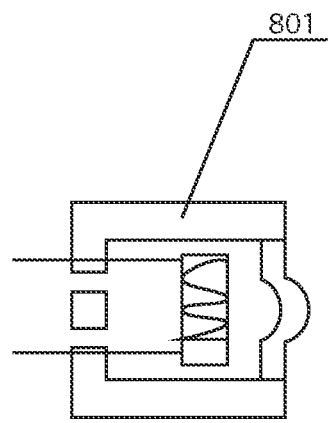
FIG. 10 is a diagram of a spray atomizer.
Figure 11:
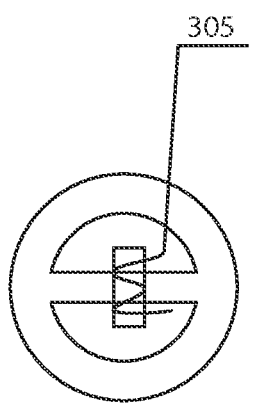
FIG. 11 is an end view of the atomizer shown in FIG. 10.

The atomizer (307) may be a capillary impregnation atomizer as in FIGS. 8 and 9, or a spray atomizer as in FIGS. 10 and 11. As shown in FIG. 4, the cigarette bottle assembly includes the cigarette liquid bottle (401), fiber (402) and suction nozzle (403). The fiber (402) containing cigarette liquid is located on one end of the cigarette liquid bottle (401). This end is inserted into the secondary shell (306) and lies against the atomizer (307). The suction nozzle (403) is located on the other end of the cigarette liquid bottle (401). Between the fiber (402) and interior wall of the cigarette liquid bottle (40 I) is an air intake hole (503).

Figure 5A:
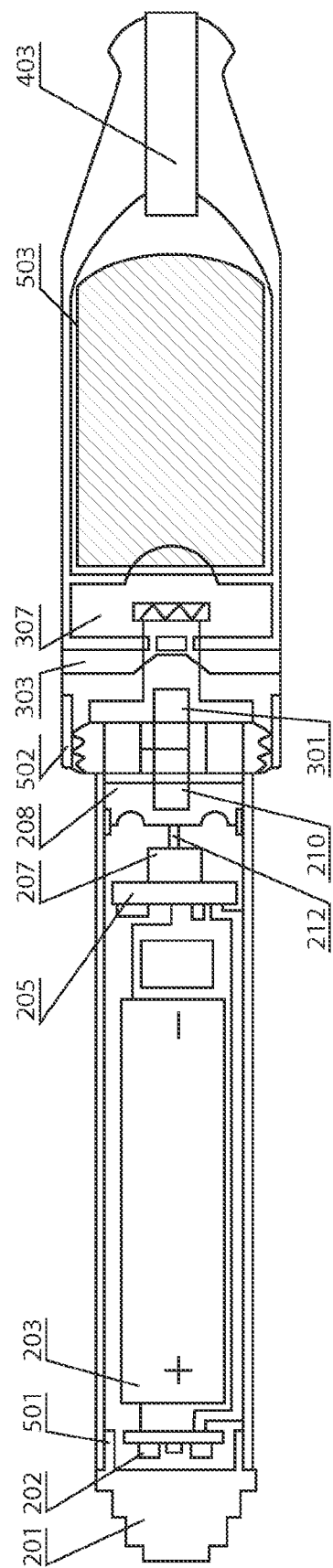
FIG. 5A is a section view of an electronic cigarette.

As shown in FIG. 5A, the standby state has the fully charged battery assembly shown on FIG. 2A fastened onto the atomizer assembly shown on FIG. 3, which is then inserted into the cigarette bottle assembly shown in FIG. 4. When the user slightly sucks the suction nozzle (403), negative pressure forms on the silica gel corrugated membrane (208) through the air intake hole (503) and the primary and secondary negative pressure cavities (210, 301). The silica gel corrugated membrane (208), under the action of suction pressure difference, distorts to drive the switch spring (212) and sensor (207), thus switching MOSFET electric circuit board (205). At this moment, the indicators (202) are lit gradually; the lithium ion battery (203) electrifies the heating body (305) inside the atomizer (307) through MOSFET electric circuit board (205) as well as the internal and external thread electrodes (302, 209).

The heating body (305) inside the atomizer (307) produces heat. The fiber (402) inside the cigarette liquid bottle (401) contains cigarette liquid, which soaks the micro-porous ceramics (801) inside the atomizer through the fiber (402). The air enters through the air intake hole (502), passes through the run-through hole on the air-liquid separator (303), and helps to form air-liquid mixture in the spray nozzle (304) of the atomizer (307). The air-liquid mixture sprays onto the heating body (305), gets vaporized, and is quickly absorbed into the airflow and condensed into aerosol, which passes through the air intake hole (503) and suction nozzle (403) to form white mist type aerosol.

When suction stops, the switch spring (212) and sensor (207) are reset; the atomizer (307) stops working; the indicators (202) gradually die down. When the operation times reaches the pre-set value, the atomizer (307) provides a work delay of 5-20 seconds per time, so as to remove the micro-dirt accumulated on the heating body (305).

Besides the micro-porous ceramics, the liquid supply material of the atomizer (307) may also be foamed ceramics, micro-porous glass, foamed metal, stainless steel fiber felt, terylene fiber, nylon fiber, nitrile fiber, aramid fiber or hard porous plastics. The heating body (305) is made of the micro-porous ceramics on which nickel-chromium alloy wire, iron-chromium alloy wire, platinum wire, or other electro thermal materials are wound. Alternatively, it may be a porous component directly made of electrically conductive ceramics or PTC (Positive Temperature Coefficient) ceramics and associated with a sintered electrode. The surface of the heating body (305) is sintered into high-temperature glaze to fix the zeolite grains, which are made of natural zeolite, artificial non-organic micro-porous ceramics or aluminum oxide grains. The cigarette liquid bottle (401) and suction nozzle (403) in the cigarette bottle assembly are made of non-toxic plastic. The fiber (402) inside of them is made of polypropylene fiber or nylon fiber to absorb cigarette liquid. In the battery assembly, there is a fine hole (501) on the indicator cap (201) for balancing the pressure difference on both sides of the silica gel corrugated membrane (208).

The cigarette liquid contains 0.1-3.5% nicotine, 0.05-5% tobacco flavor, 0.1-3% organic acid, 0.1-0.5% stabilizer, and propanediol for the remaining.

The primary and secondary shells (211, 306) are made of stainless steel tube or copper alloy tube with baked-enamel coating of real cigarette color.

Figure 12:
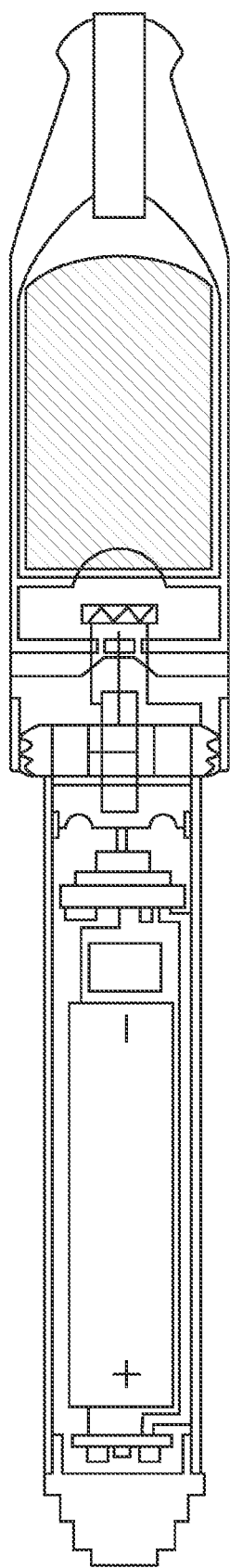
FIG. 12 is a section view of another embodiment.

As shown in FIG. 12, the diameter of the battery assembly may be increased in proportion, so that it is consistent with the diameter of the atomizer assembly. Its shell may be decorated with the leaf veins and sub-gloss brown-yellow baked-enamel coating, to create a cigar type device.

For charging the lithium ion battery (203), the screw thread electrode (601) matches the external thread electrode (209) on the battery assembly, so that it may be used as the charging interface.

The design in FIG. 2B is difference from the design in FIG. 1A as follows: Microcircuit (206) is added between MOSFET electric circuit board (205) and sensor (207). On the surface of the primary shell (211), there is a screen (204) for display of the power of the lithium ion battery (203) and the sucking times.

Figure 5B:
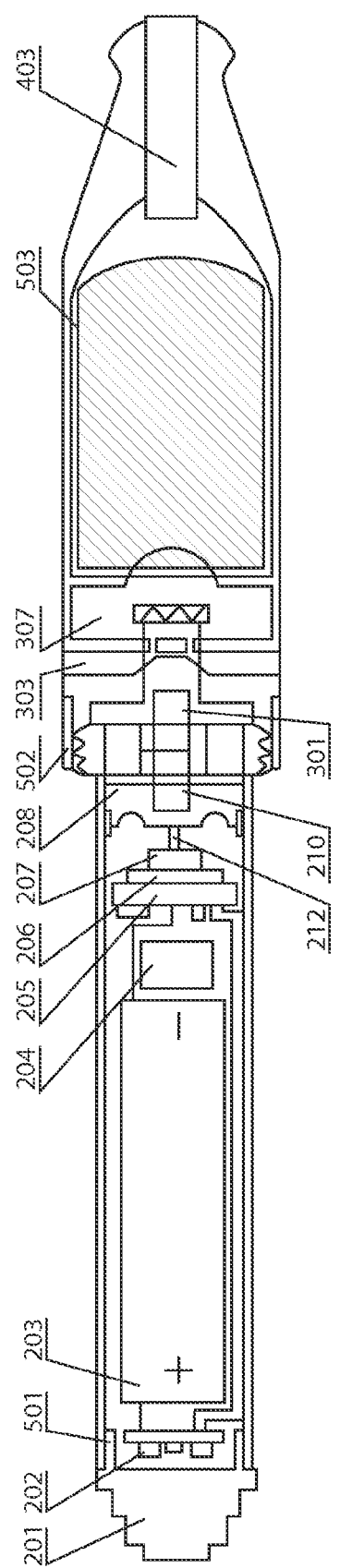
FIG. 5B is a section view of another embodiment.
Figure 6:
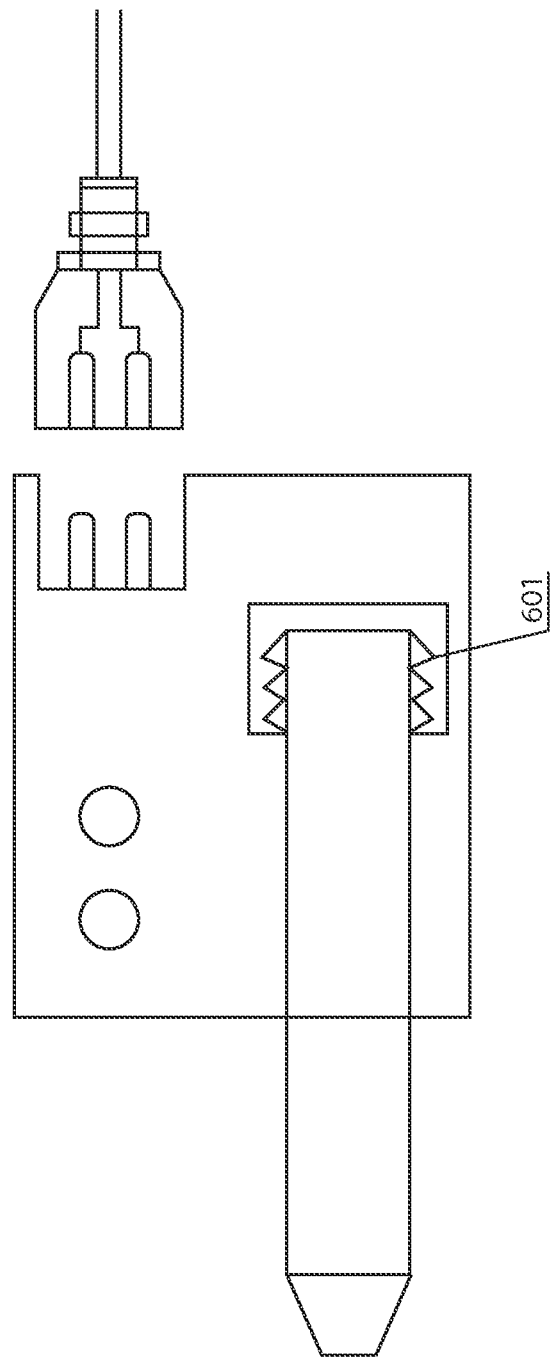
FIG. 6 is a diagram of a charger.

As shown in FIG. 5B, a fully charged battery assembly is attached onto the atomizer assembly, which is then inserted into the cigarette bottle assembly shown on FIG. 4. When the user slightly sucks the suction nozzle (403), negative pressure forms on the silica gel corrugated membrane (208) through the air intake hole (503) and the primary and secondary negative pressure cavities (210, 301). The silica gel corrugated membrane (208), under the action of suction pressure difference, distorts to drive the switch spring (212) and sensor (207), thus activating the Microcircuit (206) and MOSFET electric circuit board (205). At this moment, the indicators (202) are lit gradually; the lithium ion battery (203) electrifies the heating body (305) inside the atomizer (307) through MOSFET electric circuit board (205) as well as the internal and external thread electrodes (302, 209), so that the heating body (305) inside the atomizer (307) produces heat.

The fiber (402) inside the cigarette liquid bottle (401) contains cigarette liquid, which soaks the micro-porous ceramics (801) inside the atomizer through the fiber (402). The air enters through the air intake hole (502), passes through the run-through hole on the air-liquid separator (303), and helps to form air-liquid mixture in the spray nozzle (304) of the atomizer (307). The air-liquid mixture sprays onto the heating body (305), gets vaporized, and is quickly absorbed into the airflow and condensed into aerosol, which passes through the air intake hole (503) and suction nozzle (403) to form white mist type aerosol.

Figure 7:
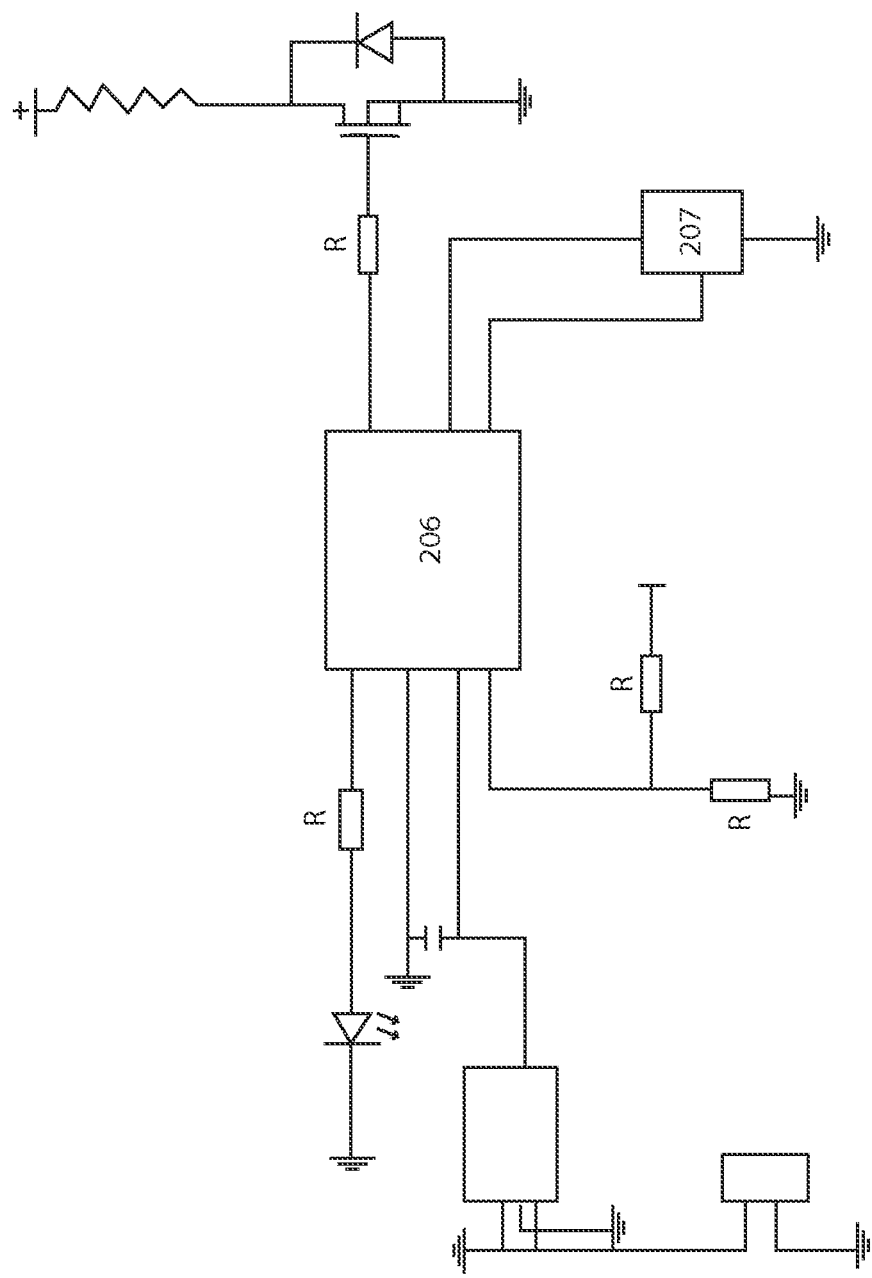
FIG. 7 is the electric circuit diagram.

As shown in FIG. 7, when the action of suction activates the sensor, Microcircuit (206) scans the sensor (207) in the power-saving mode of pulse, and according to the signal parameters of the sensor (207), restricts the atomizing capacity with the integral function of frequency to single operation time. Also, the microcircuit (206) accomplishes the pulse width modulation and over discharging protection for the constant power output, automatic cleansing for thousands of times per operation, step lighting/dying down control of the indicator, display of the operation times and battery capacity, automatic recovery after sensor malfunction shutdown, etc.

The unit and its connecting structure may also be loaded with drugs for delivery to the lung.

Above are just specifications of an example and do not necessarily restrict the scope of protection. Any equivalent modification made on the basis of the design spirit shall fall into the scope of protection.

The invention claimed is:

1. An atomizer assembly for an electronic cigarette, comprising:
    an atomizer assembly housing containing an atomizer, liquid storage, and a screw thread electrode on one end of the atomizer assembly housing, with the screw thread electrode having a through hole centered on the screw thread electrode, and
    with the atomizer in physical contact with the liquid storage; and
    a flow passageway leading from the atomizer to an outlet of the atomizer assembly housing.

2. The atomizer assembly for an electronic cigarette of claim 1 with the atomizer electrically connected to the screw thread electrode.

3. The atomizer assembly of claim 2 with the atomizer comprising a heater coil.

4. The atomizer assembly for an electronic cigarette of claim 1 with the atomizer including a heater coil wound around a porous component.

5. The atomizer assembly for an electronic cigarette of claim 4 where the porous component includes a fiber material.

6. The atomizer assembly for an electronic cigarette claim 1 with the screw thread electrode on a first end of the atomizer assembly housing and the liquid storage inserted into a second end of the atomizer assembly opposite from the first end.

7. The atomizer assembly for an electronic cigarette of claim 1 with the through hole substantially aligned with the atomizer.

8. The atomizer assembly for an electronic cigarette of claim 7 with the through hole in the screw thread electrode, the passageway and the outlet comprising a flow path through the atomizer assembly housing passing through the atomizer.

9. The atomizer assembly of claim 1 with part of the flow passageway between the liquid storage and an inside wall of the housing.

10. The atomizer assembly of claim 1 with the through-hole aligned with the atomizer.

11. An atomizer assembly for an electronic cigarette, comprising:
    an atomizer assembly housing containing an atomizer and liquid storage;
    a screw thread electrode on one end of the atomizer assembly housing;
    a through-hole in the screw thread electrode substantially aligned with the atomizer;
    the atomizer electrically connected to the screw thread electrode and with the atomizer in physical contact with the liquid storage; and
    a flow passageway leading from the atomizer to an outlet of the atomizer assembly housing.

12. The atomizer assembly for an electronic cigarette of claim 11 with the atomizer including a heater coil wound around a porous component.

13. The atomizer assembly of claim 11 with the through-hole centered in the screw thread electrode.

14. An atomizer assembly for an electronic cigarette, comprising:
    an atomizer assembly housing containing an atomizer and liquid storage;
    a screw thread electrode on one end of the atomizer assembly housing, with the atomizer electrically connected to the screw thread electrode;
    a through-hole in the screw thread electrode substantially aligned with the atomizer; and
    a flow passageway from the atomizer to an outlet of the atomizer assembly housing.

15. The atomizer assembly of claim 14 with the through-hole centered in the screw thread electrode 16. An atomizer assembly for an electronic cigarette, comprising:
    an atomizer assembly housing containing an atomizer, liquid storage, and a screw thread electrode on a first end of the atomizer assembly housing, the atomizer in physical contact with the liquid storage, and the liquid storage inserted into a second end of the atomizer assembly opposite from the first end; and
    a flow passageway leading from the atomizer to an outlet of the atomizer assembly housing.

17. The atomizer assembly of claim 16 further including a through-hole centered in the screw thread electrode.

18. The atomizer assembly of claim 16 with the through-hole aligned with the atomizer.

19. An atomizer assembly for an electronic cigarette, comprising:
    an atomizer assembly housing containing an atomizer, liquid storage, and a screw thread electrode on one end of the atomizer assembly housing, with the screw thread electrode having a through hole substantially aligned with the atomizer, and, with the atomizer in physical contact with the liquid storage; and
    a flow passageway leading from the atomizer to an outlet of the atomizer assembly housing.

20. The atomizer assembly of claim 19 with the through-hole centered in the screw thread electrode.

* * * * *